US007241902B2

(12) United States Patent
Miron et al.

(10) Patent No.: US 7,241,902 B2
(45) Date of Patent: Jul. 10, 2007

(54) ALLYLMERCAPTOCAPTOPRIL COMPOUNDS AND USES THEREOF

(75) Inventors: Talia Miron, Kfar Haim (IL); Aharon Rabinkov, Rehovot (IL); David Mirelman, Ramat Efal (IL); Meir Wilchek, Rehovot (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 305 days.

(21) Appl. No.: 10/478,396

(22) PCT Filed: May 30, 2002

(86) PCT No.: PCT/US02/16964

§ 371 (c)(1),
(2), (4) Date: Jun. 2, 2004

(87) PCT Pub. No.: WO02/096871

PCT Pub. Date: Dec. 5, 2002

(65) Prior Publication Data

US 2004/0210065 A1  Oct. 21, 2004

Related U.S. Application Data

(60) Provisional application No. 60/334,962, filed on Dec. 4, 2001, provisional application No. 60/311,829, filed on Aug. 14, 2001, provisional application No. 60/304,414, filed on Jul. 12, 2001, provisional application No. 60/293,989, filed on May 30, 2001.

(51) Int. Cl.
C07D 207/08 (2006.01)
C07D 205/04 (2006.01)
C07D 211/16 (2006.01)
C07D 223/04 (2006.01)

(52) U.S. Cl. ............. 548/540; 548/953; 546/245; 540/607

(58) Field of Classification Search ................ 548/540
See application file for complete search history.

(56) References Cited

U.S. PATENT DOCUMENTS 4,046,889 A  9/1977 Ondetti et al.
4,347,371 A * 8/1982 Iwao et al. ................ 548/201

FOREIGN PATENT DOCUMENTS

WO  WO-97/39115 A1  10/1997

OTHER PUBLICATIONS

Elkayam et al, "The Effects of Allicin and Enalapril in Fructose-Induced Hyperinsulinemic Hyperlipidemic Hypertensive Rats", Am J Hypertens 14:377-381 (2001).
Abramovitz et al "Allicin-induced decrease in formation of fatty steaks (atherosclerosis) in mice fed on a cholesterol-rich diet", Coronary Artery Disease 10 (1999) pp. 515-519.
Aquel et al "Direct relaxant effects of garlic juice on smooth and cardiac muscles" J Ethnopharmocol 33(1-2) (1991) pp. 13-19.
Auer et al "Hypertension and hyperlipidaemia: garlic helps in mild cases" Br J clin Pract Suppl 69 (1990) pp. 3-6.
Augusti et al "Lipid towering effect of allicin (diallyldisulphide-oxide on long tern feeding to normal rats" Experientia 30 (1979) pp. 369-373.
Banerjee A "Effect of aqueous extract of garlic on arterial blood pressure of normotensive and hypertensive rats" Artery 2 (1979) pp. 369-373.
Carmel et al "A flourimetric assay for angiotensin-I converting enzyme in human serum" Clinica Chimica Acta 93 (1979) pp. 215-220.
Cushman et al "History of the design of captopril and related inhibitors of angiotensin converting enzyme" Hypertension 17 (1991) pp. 589-592.
Eliat et al "Alteration of lipid profile in hyperlipidemic rabbits by allicin, an active constituent of garlic" Coronary Artery Dis 6 (1995) pp. 985-990.
Ehrlich et al "Contribution of nitric oxide to the beneficial effects of enalapril in the fructose-induced hyperinsulinemic rat" Hypertension 28 (1996) pp. 754-757.
Ehrlich et al "Efffect of angiotensin-converting enzyme inhibitors of fructose induced hypertension and hyperinsulinaemia in rats" Clin Exp Pharmocol Physiol 22 (Sup1) (1996) pp. s347-s349.
Foushee et al., "Garlic as a natural agent for the treatment of hypertension: a preliminary" Cytobios 34 (135-36) (1982) pp. 145-152.
Lawson LD in Phytomedicines of Europe: Their Chemistry and Biological Activity (Lawson et al eds.) vol. 691, pp. 176-209, American Chemical Society, Washington (1998).
Malik et al "Hypotensive effect of freeze-dried garlic (Allium sativum) sap in dog" PMA J pak Med Assoc 31 (1981) pp. 12-13.
Materson et al "Angiotensin-converting enzyme inhibitors in hypertension. A dozen years of experience" Arch Intern Med 1544 (1994) pp. 513-523.
Migdalof et al "Captopril: pharmacology, metabolism and disposition" Drug Metab Rev 15 (1984) pp. 841-869.
Miron et al "The mode of action of allicin: its ready permeability through phospholipid membranes may contribute to its biological activity" Biochim Biophys Acta 1463 (2000) pp. 20-30.
Ondetti et al., "Design of specific inhibitors of angiotensin-converting enzyme: new class of orally active antihypertensive agents" Science 196 (1977) pp. 441-444.
Petkov U "Plants with hypotensive, antiatheromatous and coronarodilating action" Am J of Chinese Medicine 7 (1979) pp. 197-236.

(Continued)

Primary Examiner—Kamal A. Saeed
Assistant Examiner—Shawquia Young
(74) Attorney, Agent, or Firm—Browdy and Neimark PLLC

(57) ABSTRACT

Compounds which are the reaction product of allicin and ACE-inhibiting compounds are useful in treating hypertension, elevated triglycerides, and elevated insulin.

22 Claims, 5 Drawing Sheets

OTHER PUBLICATIONS

Rabinkov et al "The mode of action of allicin: trapping radicals and interaction with thiol containing proteins" Biochim Biophys Acta 1379 (1998) pp. 233-244.

Reaven et al "Sugar-induced hypertension in Sprague-Dawley rats" Am J Hypertens 4 (7 Pt 1) (1991) pp. 610-614.

Ruffin et al "An evaluation of the side effects of garlic as an antihypertensive agent" Cytobios 37 (146) (1983) pp. 85-89.

Thind GS "Angiotensin converting enzyme inhibitors: comparative structure, pharmacokinetics, and pharmacodynamics" Cardiovasc Drugs Ther 4 (1990) pp. 199-206.

* cited by examiner

The effect of CPSSA and captopril on blood pressure in rats. Rats were fed 5 weeks with fructose rich diet. The rats, after 3 weeks of diet, were treated with either CPSSA 40 mg/kg [ ▨ ], 56mg/kg [ ▨ ] or captopril 80 mg/kg [ ▨ ] in the drinking water. The control group [ ☐ ] was fed with fructose rich diet only.

The effect of CPSSA and captopril on triglycerides level in rats sera. Rats were fed 5 weeks with fructose rich diet. The rats, after 3 weeks of diet, were treated with either CPSSA 40 mg/kg [▨], 56mg/kg [▨] or captopril 80 mg/kg [▧] in the drinking water. The control group [☐] was fed with fructose rich diet only.

The effect of CPSSA and captopril on insulin level in rats sera. Rats were fed 5 weeks with fructose rich diet. The rats, after 3 weeks of diet, were treated with either CPSSA 40 mg/kg [▨], 56mg/kg [▨] or captopril 80 mg/kg [▨] in the drinking water. The control group [☐] was fed with fructose rich diet only.

ALLYLMERCAPTOCAPTOPRIL COMPOUNDS AND USES THEREOF

FIELD OF THE INVENTION

The present invention relates to allylmercaptocaptopril and derivatives thereof which are useful in treating hypertension, elevated triglycerides and hyperglycemia.

BACKGROUND OF THE INVENTION

Captopril (D-3-mercapto-2-methylpropanoyl-L-proline) and related azetidine and proline derivatives are competitive inhibitors of angiotensin-converting enzyme (ACE) that block the conversion of angiotensin I to angiotensin II. Captopril and its derivatives are used as antihypertensive agents in treating most forms of hypertension (U.S. Pat. No. 4,046,889, Ondetti et al, 1977; Thind, 1990; Cushman et al, 1991. Migdalof et al. 1984; Materson et al, 1994)

Captopril contains a free sulfhydryl group and is quite stable in aqueous solution. However, in the blood or plasma of mammals, including humans, it is rapidly oxidized to its disulfide dimer and is involved in other disulfide exchange reactions. Captopril was found to bind covalently but reversibly to plasma proteins, cysteine, and glutathione (Migdalof et al, 1984)

Unfortunately, rather high doses of captopril are required to reduce blood pressure. This phenomenon may be because most of the captopril is used up in reactions with serum protein, to reduce —S—S bonds in proteins, and to form the mixed disulfide of protein-captopril. Thus, only a small amount of free captopril, or captopril recycled from the mixed disulfide with proteins, glutathione, and cysteine, remains for inhibiting ACE. Therefore, larger amounts of captopril are required as compared with other non-thiol containing ACE inhibitors. This may explain the discrepancy between the in vitro and in vivo activity of captopril.

It has recently been shown that allicin (dithiosulfinate), a product of crushed garlic, which the present inventors prepared semi-synthetically (international patent WO 97/39115), also possesses antihypertensive properties. Other studies reported the remedial effects of allicin on cardiovascular risk factors, mainly on serum cholesterol, triglycerides levels, as well as lipoprotein balance, streak formation, and thrombogenesis in animals and in humans (Augusti et al, 1974; Eilat et al, 1995; Lawson, 1998; Abramovitz et al, 1999). Lipid lowering effect is one of the earliest established properties of garlic preparations, which also have a hypotensive effect as shown by Loeper et al (1921), which effect was confirmed by others in humans (Damrau, 1941; Petkov, 1979) and in animals (Chanderkar et al, 1973; Banerjee, 1979; Malik et al, 1981; Foushee et al, 1982; Ruffin et al, 1983; Auer et al, 1990; Aqel et al, 1991).

Two possible mechanisms for the action of allicin have been suggested. One involves the antioxidant activity of allicin, while the other mechanism is that the particular structure of allicin, as activated disulfide, makes it a good candidate for interaction with the SH groups of proteins and low molecular weight thiols. Allicin, which is a very reactive compound, also disappears within a few minutes after being mixed with blood, due to its fast penetration through cell membranes, and its reaction with free thiol containing compounds, mainly reduced glutathione (GSH). From studies conducted by the present inventors, Rabinkov et al (1998) and Miron et al (2000), it appears that the active principal of allicin is the allylmercapto moiety (AM), which blocks thiol containing enzymes or reacts as a very efficient antioxidant.

SUMMARY OF THE INVENTION

It is an object of the present invention to overcome the aforesaid deficiencies in the prior art.

It is another object of the present invention to produce compounds which have hypotensive effects.

It is a further object of the present invention to produce compounds which lower triglycerides and insulin.

The compounds of the present invention have the formula

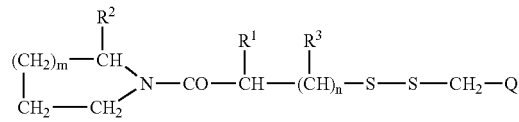

wherein:
$R^1$ and $R^3$ are each hydrogen, lower alkyl, or phenyl-lower alkyl;
$R^2$ is hydrogen, hydroxy, lower alkyl or carboxyl;
Q is —CH=CH$_2$ or —C≡CH;
m is 0–10; and
n is 0, 1, or 2.

Pharmaceutical compositions for treating hypertension include the compounds of the present invention, as active principle, along with a suitable pharmaceutically acceptable excipient or carrier. The active principle is present in an amount effective to reduce blood pressure.

The present invention further comprehends methods for treating hypertension by administering to a patient in need of reduction of hypertension an effective amount of a compound or composition of the present invention. Methods of treating elevated triglycerides and/or elevated insulin levels by administering such compounds or compositions are also encompassed by the present invention.

The present invention also includes a method for preparing the compounds of the present invention by reacting an HCE-inhibiting proline derivative compound with allicin or a derivative thereof.

The nature and objects of the present invention will be better understood upon consideration of the following detailed-description in conjunction with the drawings.

DETAILED DESCRIPTION OF THE INVENTION

Figure 1:
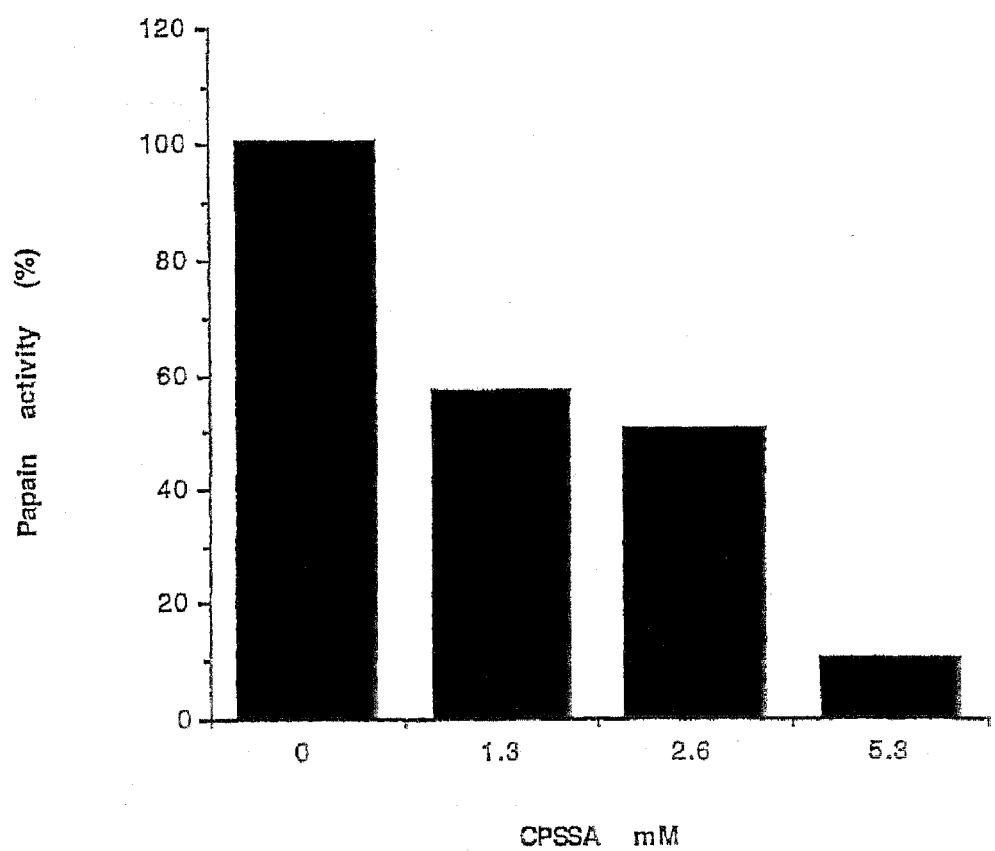
FIG. 1 illustrates inhibition of papain activity by CPSSA at various concentrations.

The compounds of the present invention inhibit the conversion of the decapeptide angiotensin I to angiotensin II, and therefore they are useful in reducing or relieving angiotensin related hypertension, and in reducing triglycerides and insulin levels. The action of the enzyme renin on angiotensinogen, a pseudoglobulin in blood plasma, produces angiotensin I. Angiotensin I is converted by angiotensin converting enzyme (ACE) to angiotensin II, which is an active pressor substance which has been implicated as the causative agent in various forms of hypertension in many mammalian species. The compounds of the present invention intervene in the renin→angiotensin I→angiotensin II sequence by inhibiting angiotensin converting enzyme and reducing or eliminating the formation of the pressor substance angiotensin II. Thus, by administering a composition containing at least one of the compounds of the present invention, angiotensin dependant hypertension can be alleviated.

The compounds of the present invention combine the advantages of ACE-inhibiting azetidine and proline derivatives with the advantages of allicin, both of which are effective agents against hypertonia, each compound operating by a different mechanism. The product of the reaction between captopril per se and allicin is allylmercaptocaptopril (CPSSA), a non-symmetric disulfide (Scheme 1) which combines both the specific pharmacological activity of captopril and the beneficial properties of diallyldithiosulfinate (allicin)

More generally, when Q is either allyl or propargyl, the following reaction occurs:

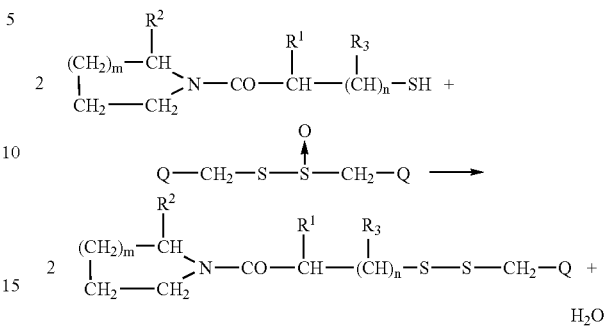

where
$R^1$ is hydrogen, lower alkyl or phenyl-lower alkyl;
$R^2$ is hydrogen, hydroxy, lower alkyl, $R_3CO$, or carboxyl;
$R^3$ is hydrogen, lower alkyl or phenyl-lower alkyl;
m is 0–10; and
n is 0, 1, or 2.

Scheme 1

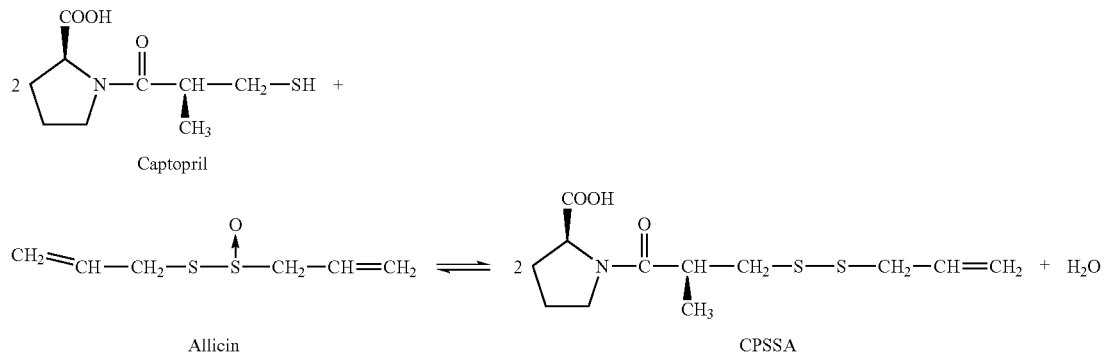

Additionally, diners and derivatives of allicin, such as ajoine, which also react with thiols, can be used to prepare ACE-inhibiting compounds according to the present invention. For purposes of the present invention, "derivatives of allicin" refers to diners, trimers, etc. as well as allicin compounds in which one or more of the carbon atoms are substituted which react with thiols.

Compounds according to the present invention can also be prepared from the acetyleno (propargyl) analogue of allicin,

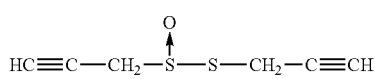

Dipropargyldithiosulfinate.

This propargyl analogue can be used to prepare the propargyl derivative of captopril, propargylmercaptocaptopril, as it performs the same thiolation reaction.

The stereoisomers in which m is 1 and proline is in the L-form are especially preferred.

The lower alkyl groups represented by any of the variables include straight and branched chain $C_1$–$C_6$ hydrocarbon radicals, such as methyl, ethyl, propyl, isopropyl, butyl, isobutyl, t-butyl, pentyl, isopentyl, hexyl, and the like. The lower alkoxy groups are of the same kind having from 1 to 7 carbon atoms linked to oxygen, such as methoxy, ethoxy, propoxy, isopropoxy, butoxy, isobutoxy, t-butoxy, and the like. The $C_1$–$C_4$ members of this group, particularly the $C_1$ and $C_2$ members, of both types are preferred. Phenylmethyl is the preferred phenyl-lower alkyl group.

The lower alkanoyl groups are those which have acyl radicals of the lower ($C_2$–$C_7$) fatty acids, such as acetic, propionyl, butyryl, isobuytyryl, and the like. Similarly, those lower alkanoyl groups having up to four carbon atoms, and particularly acetyl, are preferred.

Captopril and its derivatives can be prepared by methods disclosed in U.S. Pat. No. 4,046,889, the entire contents of which being hereby incorporated by reference.

CPSSA and its derivatives and related compounds react very sluggishly with serum proteins where the thiol groups are mostly in the disulfide form. Thus, the compounds of the present invention are stable in blood or plasma of mammals and high doses of the compounds are not needed to produce an anti-hypertensive effect.

Compositions within the scope of the present invention include all compositions wherein the active ingredient is contained in an amount effective to achieve its intended purpose. While individual needs vary, determination of optimal ranges of effective amounts of each compound is within the skill of the art. Typical dosages comprise 0.01 to 100 mg/kg body weight. The preferred dosages comprising 0.1 to 100 mg/kg body weight. The most preferred dosages comprise 1 to 50 mg/kg body weight.

Pharmaceutical compositions for administering the active ingredients of the present invention preferably contain, in addition to the pharmacologically active compound, suitable pharmaceutically acceptable carriers comprising excipients and auxiliaries which facilitate processing of the active compounds into preparations which can be used pharmaceutically. Preferably, the preparations, particularly those preparations which are administered orally and which can be used for the preferred type of administration, such as tablets, dragees, and capsules, and also preparations which can be administered rectally, such as suppositories, as well as suitable solutions for administration by injection or orally, contain from about 0.01 to about 99 percent by weight, preferably from about 20 to 75 percent by weight, active compound(s), together with the excipient. For purposes of the present invention, all percentages are by weight unless otherwise indicated. In addition to the following described pharmaceutical composition, the compounds of the present invention can be formulated as inclusion complexes, such as cyclodextrin inclusion complexes.

Examples of pharmaceutically acceptable acid addition salts for use in pharmaceutical compositions according to the present invention include those derived from mineral acids, such as hydrochloric, hydrobromic, phosphoric, metaphosphoric, nitric, and sulfuric acids, and organic acids such as tartaric, acetic, citric, malic, lactic, fumaric, benzoic, glycolic, gluconic, succinic, and arylsulfonic, such as p-toluenesulfonic, acids.

The pharmaceutically acceptable carriers include vehicles, adjuvants, excipients, or diluents that are well known to those skilled in the art and which are readily available. It is preferred that the pharmaceutically acceptable carrier be one which is chemically inert to the active compounds and which has no detrimental side effects or toxicity under the conditions of use.

The choice of carrier is determined partly by the particular active ingredient, as well as by the particular method used to administer the composition. Accordingly, there is a wide variety of suitable formulations of the pharmaceutical compositions of the present invention. Formulations can be prepared for oral, aerosol, parenteral, subcutaneous, intravenous, intraarterial, intramuscular, intraperitoneal, intratracheal, rectal, and vaginal administration.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste using, for example, maize starch, wheat starch, rice starch, potato starch, gelatin, tragacanth, methyl cellulose, hydroxypropylmethylcellulose, sodium carboxymethylcelullose, and/or polyvinyl pyrrolidine.

Suitable formulations for parenteral administration include aqueous solutions of the active compounds in water-soluble form, such as water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions may contain substances which increase the viscosity of the suspension, including, for example, sodium carboxymethyl cellulose, sorbitol, and/or dextran. Optionally, the suspension may also contain stabilizers.

Other pharmaceutically acceptable carries for the active ingredients according to the present invention are liposomes, pharmaceutical compositions in which the active ingredient is contained either dispersed or variously present in corpuscles contained either dispersed or variously present in corpuscles consisting of aqueous concentric layers adherent to lipid layers. The active ingredient may be present both in the aqueous layer and in the lipidic layer, inside or outside, or, in any event, in the non-homogeneous system generally known as a liposomic suspension.

The hydrophobic layer, or lipid layer, generally, but not exclusively, comprises phospholipids such as lecithin and sphingomyelin, steroids such as cholesterol, more or less ionic surface active substances such as dicetyl phosphate, stearylamine, or phosphatidic acid, and/or other materials of a hydrophobic nature.

The compounds may also be formulated for transdermal administration, for example in the form of transdermal patches so as to achieve systemic administration. Formulations suitable for oral administration can consists of liquid solutions such as effective amounts of the compound(s) dissolved in diluents such as water, saline, or orange juice; capsules, tables, sachets, lozenges, and troches, each containing a predetermined amount of the active ingredient as solids or granules; powders, suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents. Capsule forms can be of the ordinary hard- or soft-shelled gelatin type containing, for example, surfactants, lubricant, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscaramellose sodium, talc, magnesium stearate, calcium stearate, zinc stearate, stearic acid, and other preservatives, flavoring agents, and pharmaceutically acceptable disintegrating agents, moistening agents preservatives flavoring agents, and pharmacologically compatible carriers. Lozenge forms can comprise the active ingredient in a carrier, usually sucrose and acacia or tragacanth, as well as pastilles comprising the active ingredient in an inert base such as gelatin or glycerin, or sucrose and acacia. Emulsions and the like can contain., in addition to the active ingredient, such carriers as are known in the art.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds can be administered in a physiologically acceptable diluent in a pharmaceutical carriers, such as a sterile liquid or mixture of liquids, including water, saline, aqueous dextrose and related sugar solutions, an alcohol such as ethanol, isopropanol, or hexadecyl alcohol, glycols such as propylene glycol or polyethylene glycol, glycerol ketals such as 2,2-dimethyl-1,3-dioxolane-4-methanol, ethers such as poly(ethylene glycol) 400, oils, fatty acids, fatty acid esters or glycerides, or acetylated fatty acid glycerides, without the addition of a pharmaceutically acceptable surfactants, such as soap or a detergent, suspending agent, such as carbomers, methylcellulose, hydroxypropylmethylcellulose, or carboxymethylcellulose, or emulsifying agents and other pharmaceutical adjuvants.

Oils which can be used in parenteral formulations include petroleum, animal, vegetable, or synthetic oils. Specific examples of oils include peanut, soybean, sesame, cottonseed, corn, olive, petrolatum, and mineral. Fatty acids can be used in parenteral formulations, including oleic acid, stearic acid, and isostearic acid. Ethyl oleate and isopropyl myristate are examples of suitable fatty acid esters. Suitable salts for use in parenteral formulations include fatty alkali metal, ammonium, and triethanolamine salts, and suitable detergents include cationic detergents such as dimethyl dialkyl ammonium halides, and alkyl pyridimium halides; anionic detergents such as dimethyl olefin sulfonates, alkyl, olefin, ether, and monoglyceride sulfates and sulfosuccinates; polyoxyethylenepolypropylene copolymers; amphoteric detergents such as alkyl-beta-aminopropionates and 2-alkyl-imidazoline quaternarry ammonium salts; and mixtures thereof.

Parenteral formulations typically contain from about 0.5 to 25% by weight of the active ingredient in solution. Suitable preservatives and buffers can be used in these formulations. In order to minimize of eliminate irritation at the site of injection, these compositions may contain one or more nonionic surfactants having a hydrophilic-lipophilic balance (HLB) of from about 12 to about 17. The quantity of surfactant in such formulations ranges from about 5 to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be present in unit dose or multiple dose sealed containers, such as ampules and vials, and can be stored in a freeze-dried (lyophilized) condition requiring only the addition of the sterile liquid carrier, e.g., water, for injections immediately prior to use. Extemporaneous injection solutions and suspensions can be prepared from sterile powders, granules, and tablets of the kind previously described.

Additionally, the active ingredients can be formulated into suppositories by mixing the active ingredient with a variety of bases, including emulsifying bases or water-soluble bases. Formulations suitable for vaginal administration may be in the form of pessaries, tampons, creams, gels, pastes, foam, or spray formulations containing, in addition to the active ingredient, such carriers as are known in the art to be appropriate.

The active ingredients can be used as functionalized congeners for coupling to other molecules, such as amines and peptides. The use of such congeners provides for increased potency, prolonged duration of action, and pro-drugs. Water solubility is also enhanced, which allows for reduction, if not complete elimination, of undesirable binding to plasma proteins and partition in to lipids. Accordingly, improved pharmacokinetics can be realized.

Any number of assays well known in the art, such as that of Carmel et al (1979), may be used to test whether a particular compound suspected of being an ACE inhibitor is effective as such.

In determining the dosages of the compounds to be administered, the dosage and frequency of administration is selected in relation to the pharmacological properties of the specific active ingredients. Normally., at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the $ID_{50}$ level of the active ingredient in question can be one of the dosage levels selected, and the other two selected to reach a toxic level. The lowest dose that dose not exhibit a biologically demonstrable effect. The toxicology tests should be repeated using appropriate new doses calculated on the basis of the results obtained. Young, healthy mice or rats belonging to a well-defined strain are the first choice of species, an the first studies generally use the preferred route of administration. Control groups given a placebo or which are untreated are included in the tests. Tests for general toxicity, as outlined above, should normally be repeated in another non-rodent species, e.g., a rabbit or dog. Studies may also be repeated using alternate routes of administration.

Singe dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds. Data on single dose toxicity, e.g., $ID_{50}$, the dosage at which half of the experimental animals die, is to be expressed in units of weight or volume per kg of body weight and should generally be furnished for at least two species with different modes of administration. In addition to the $ID_{50}$ value in rodents, it is desirable to determine the highest tolerated dose and/or lowest lethal dose for other species, i.e., dog and rabbit.

When a suitable and presumably safe dosage level has been established as outlined above, studies on the drug's chronic toxicity, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed. Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The compounds of the present invention are then ready for clinical trials to compare the efficacy of the compounds to existing therapy. A dose-response relationship to therapeutic effect and for side effects can be more finely established at this point.

The amount of compounds of the present invention to be administered to any given patient must be determined empirically, and will differ depending upon the condition of the patients. Relatively small amounts of the active ingredient can be administered at first, with steadily increasing dosages if no adverse effects are noted. Of course, the maximum safe toxicity dosage as determined in routine animal toxicity tests should never be exceeded.

The compounds of the present invention can be administered in a single dose, or preferably two or four daily doses, provided on the basis of about 0.01 to 50 mg per kilogram per day, preferably about 0.1 to about 25 mg per kilogram per day, to reduce blood pressure. The compounds are preferably administered orally, but parenteral routes, such as subcutaneously, intramuscularly, intravenously, or intraperitoneally, can also be used.

The compounds of the present invention formulated in compositions such as tablets, capsules, or elixirs for oral administration, or in sterile solutions or suspensions for parenteral administration. About 1 to about 250 mg of a compound or mixture of compounds is compounded with a pharmaceutically acceptable vehicle, carrier, excipient, binder, preservative, stabilizer, flavor, etc., in a unit dosage form. The amount of active substance in these compositions or preparations is such that a suitable dosage in the range indicated is obtained.

Materials and Methods

Pure allicin was produced by interaction of the synthetic substrate allicin with stabilized alliinase as described previously in Mirelman et al, international patent WO 97/39115. Fructose was purchased from Harlan, Teklad (Madison, Wis.). Captopril was purchased form Sigma, St. Louis, Mo. Sprague-Dawley rats were purchased form ANILAB, Tal-Shahar, Israel.

Captopril, allylmercaptocaptopril, and allicin were separated by HPLC using an LKB HPLC system with an SP 4290 integrator (Spectraphysics). Separation was effected on a LiChrosornb RP-18 (7 mm) column using 60% methanol in water containing 0.1% formic acid or 0.05% trifluoroacetic acid as an eluant. The flow rate was 0.55 ml/minute.

CPSSA (0–5 mM) modification of activated and gel-filtered papain was conducted at room temperature in 50 mM sodium acetate, 2 mM EDTA pH 6.1. The inhibited papain was reactivated with 5 mM reduced glutathione.

The activity of angiotensin-converting enzyme was assayed according to Carmel et al (1979).

Animal experiments were conducted on Sprague-Dawley rats according to Reaven's model (Reaven et al, 1991), in which rats feeding on a fructose-enriched diet developed high blood pressure as well as high insulin and high triglyceride levels. This model was previously used to test the effect of different angiotensin-converting enzyme inhibitors on metabolic parameters and blood pressure Erlich et al (1995), Erlich et al (1996). In the present study, the effects of CPSSA and captopril on blood pressure, as well as serum levels of triglycerides and insulin, were compared.

RESULTS

EXAMPLE 1

Synthesis and Isolation of S-allylmercaptocaptopril (CPSSA)

The reaction of allicin and captopril was performed as follows:

Captopril (217 mg, 1 mmole) in 7.5 ml water pre-adjusted to pH 5.5, was added dropwise to allicin (90 mg, 0.55 mmole) dissolved in 3 ml absolute ethanol. The reaction mixture was magnetically stirred for 15–20 minutes at room temperature. Excess allicin was extracted by ether, and the water phase was acidified with HCL and extracted with ethyl acetate. The organic phase was dried by rotor evaporation, re-dissolved either in ethanol and dried by Speed Vac centrifugation or re-dissolved in water and dried by lyophilization. The yield of the reaction was 90%. The reaction product was detected by HPLC analysis (RT 14.1 minutes). The structure was confirmed by NMR and MS.

EXAMPLE 2

SH Modification of Papain

Incubation of papain with allylmercaptocaptopril caused a significant decrease of enzyme activity. The degree of inhibition was concentration dependent. The activity of the inactivated papain could be restored by reduced glutathione.

Activated papain was mixed with various concentrations of CPSSA for 10 minutes at room temperature in 50 mM sodium acetate, 2 mM EDTA buffer, pH 6.5. The residual enzyme activity was measured by monitoring the rate of hydrolysis of the substrate benzoyl arginine-p-nitro anilide at 382 nm. The results are shown in FIG. 1.

EXAMPLE 3

Effect of CPSSA on Angiotensin Converting Enzyme Activity In Vitro

Figure 2:
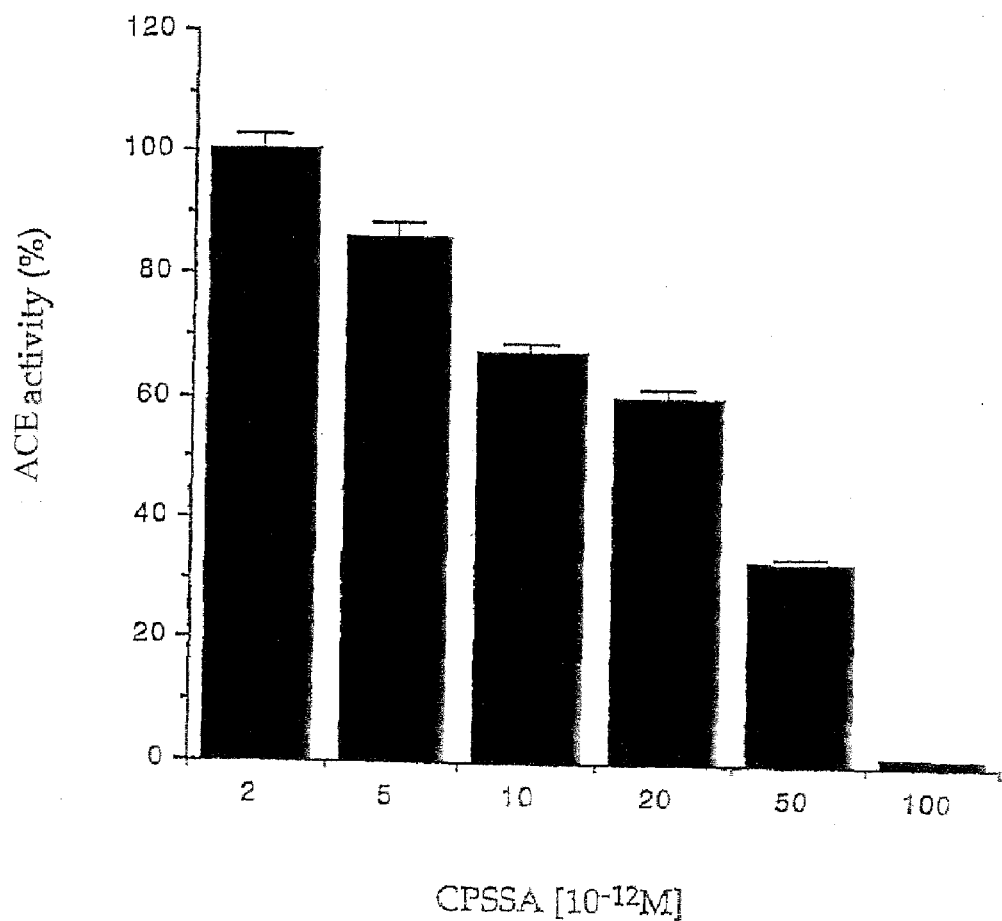
FIG. 2 shows inhibition of ACE by various concentrations of CPSSA.

In order to determine if CPSSA reacts in a similar way to captopril, which inhibits the activity of angiotensin converting enzyme, serial dilutions of CPSSA were prepared. Samples were added to a reference serum and the activity of the enzyme was monitored as shown in FIG. 2. The inhibition was concentration dependant and essentially does not differ from the inhibition profile obtained with captopril.

EXAMPLE 4

Figure 3:
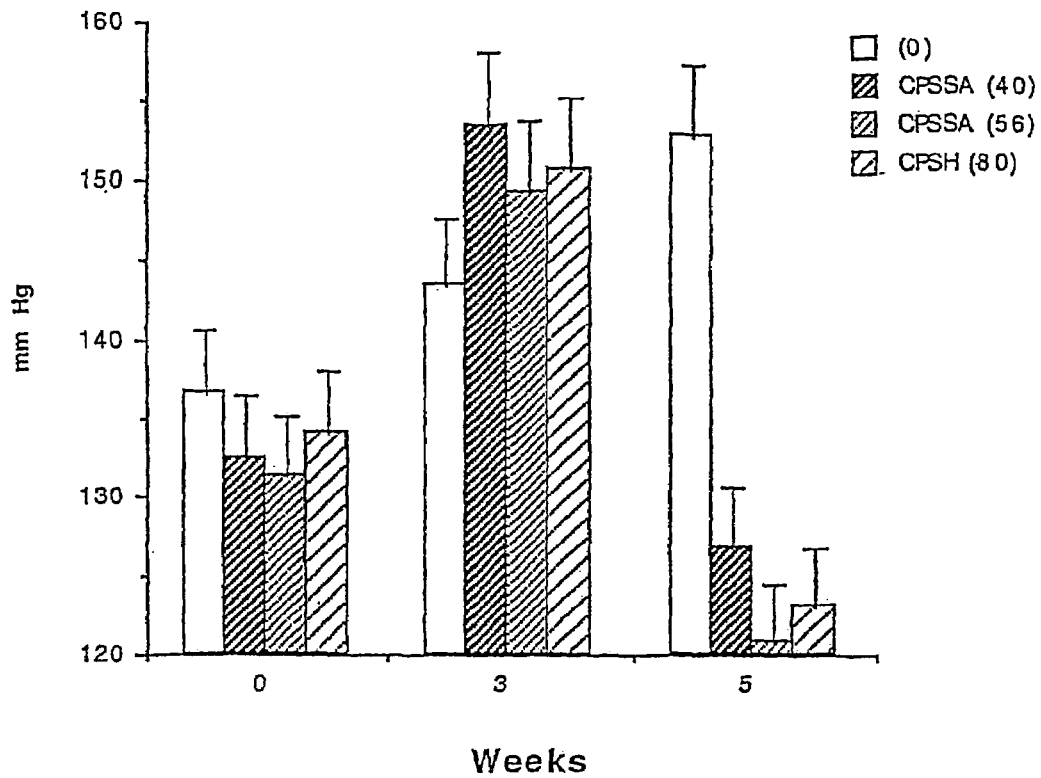
FIG. 3 illustrates the effect of CPSSA and captopril on blood pressure in rats.
Figure 4:
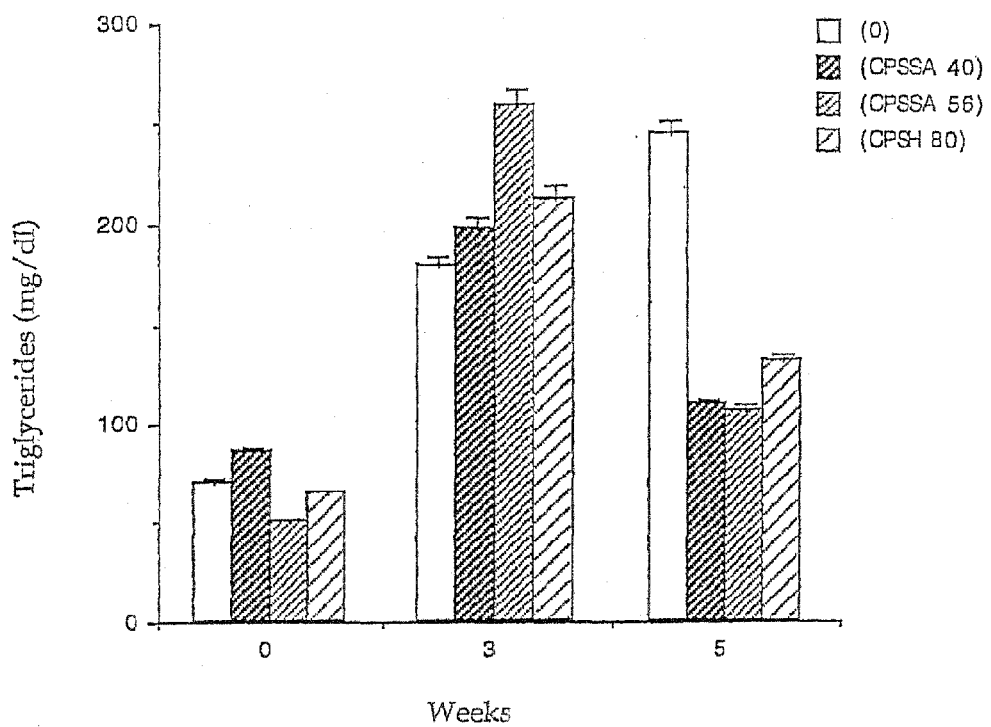
FIG. 4 shows the effect of CPSSA and captopril on triglycerides level in rats' sera.
Figure 5:
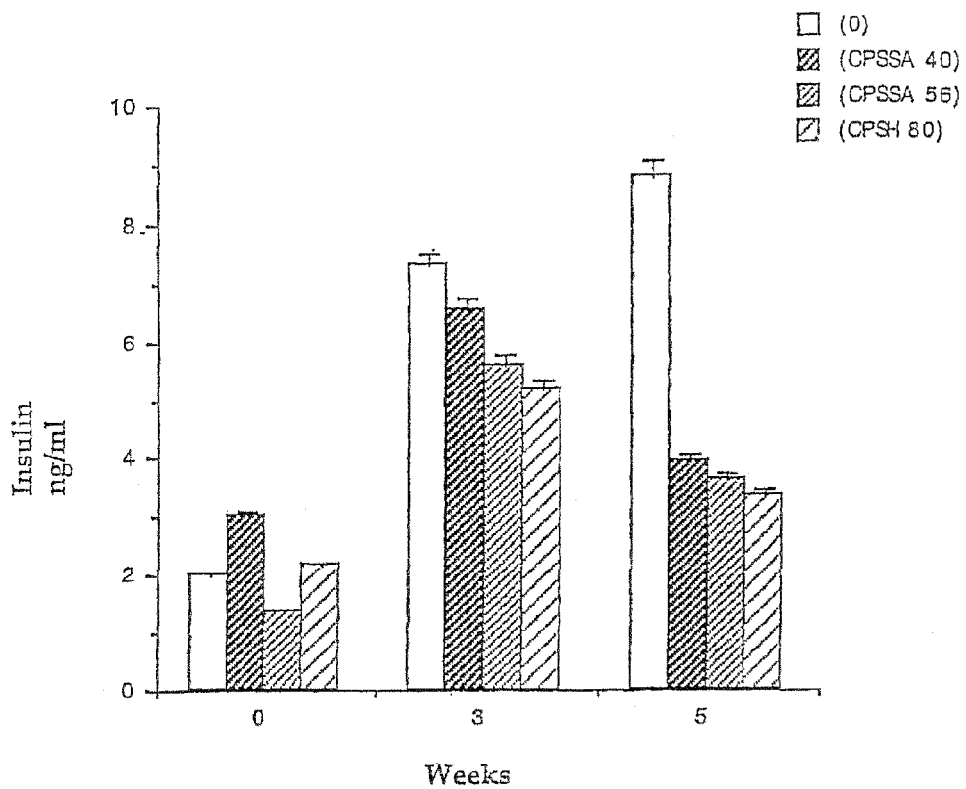
FIG. 5 shows the effect of CPSSA and captopril on insulin level in rats' sera.

Effect of CPSSA on Blood Pressure, Serum Triglycerides, Insulin Concentrations, and Body Weight Model Sprague-Dawley male rates, five rats/group, 220–240 g body weight, were fed with a fructose-rich diet for three weeks, followed by two weeks of treatment with either CPSSA or captopril predissolved in the drinking water in doses of CPSSA of 40 and 57 mg/kg and 80 mg/kg captopril, together with the fructose-rich diet. The control group was fed only the fructose-rich diet. Measurements of body weight, blood pressure, serum levels of triglycerides and insulin were conducted at 0, 3, and 5 weeks into the treatment. As can readily be seen from FIGS. 3–5, CPSSA significantly decreased blood pressure (FIG. 3) and reduced the serum levels of triglycerides (FIG. 4) and insulin (FIG. 5) to near normal levels once administration of CPSSA occurred. Similar results were obtained with captopril with doses that were nearly double that of CPSSA. CPSSA, like captopril, decreased serum insulin levels to normal values in model animals (FIG. 5), but CPSSA appears to be more active than captopril in decreasing levels of triglycerides (FIG. 4). No effects on body weight were found in either treatment.

Pharmaceutical compositions according to the present invention can be administered by any convenient route, including parenteral, subcutaneous, intravenous, intramuscular, intraperitoneal, or transdermal. Alternatively or concomitantly, administration may be by the oral route. The dosage administered depends upon the age, health, and weight of the recipient, nature of concurrent treatment, if any, and the nature of the effect desired.

The foregoing description of the specific embodiments will so fully reveal the general nature of the invention that others can, by applying current knowledge, readily modify and/or adapt for various applications such specific embodiments without undue experimentation and without departing from the generic concept. Therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying our various disclosed functions may take a variety of alternative forms without departing from the invention. Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or not precisely equivalent to the embodiment or embodiments disclosed in the specification above; and it is intended that such expressions be given their broadest interpretation.

REFERENCES

Abramovitz et al, "Allicin-induced decrease in formation of fatty steaks (atherosclerosis) in mice fed on a cholesterol-rich diet", *Coronary Artery Disease* 10:515–519 (1999)

Aqel et al, "Direct relaxant effects of garlic juice on smooth and cardiac muscles", *J Ethnopharmacol* 33(1–2):13–19 (1991)

Auer et al, "Hypertension and hyperlipidaemia: garlic helps in mild cases", *Br J Clin Pract Suppl* 69:3–6 (1990)

Augusti et al, "Lipid lowering effect of allicin (diallyl disulphide-oxide on long term feeding to normal rats" *Experientia* 30:468–470 (1974)

Banerjee A, "Effect of aqueous extract of garlic on arterial blood pressure of normotensive and hypertensive rats", *Artery* 2:369–373 (1979)

Carmel et al, "A fluorimetric assay for angiotensin-I converting enzyme in human serum", *Clinica Chimica Acta* 93:215–220 (1979)

Chanderkar et al, "Analysis of hypotensive action on *Allium sativum* (garlic)", *Indian Journal of Pysiology and Pharmacology* 17:132–133 (1973)

Cushman et al, "History of the design of captopril and related inhibitors of angiotensin converting enzyme", *Hypertension* 17:589–592 (1991)

Damrau F, "The use of garlic concentrate in vascular hypertension", *Medical Record* 153:249–251 (1941)

Eilat et al, "Alteration of lipid profile in hyperlipidemic rabbits by allicin, an active constituent of garlic", *Coronary Artery Dis* 6:985–990 (1995)

Ehrlich et al, "Effect of angiotensin-converting enzyme inhibitors on fructose induced hypertension and hyperinsulinaemia in rats", *Clin Exp Pharmacol Physiol* 22(Sup 1):S347–S349 (1995)

Ehrlich et al, "Contribution of nitric oxide to the beneficial effects of enalapril in the fructose-induced hyperinsulinemic rat", *Hypertension* 28:754–757 (1996)

Foushee et al, "Garlic as a natural agent for the treatment of hypertension: a preliminary", *Cytobios.* 34 (135–36):145–152 (1982)

Lawson L D in *Phytomedicines of Europe: Their Chemistry and Biological Activty* (Lawson et al eds.), Vol. 691, pp. 176–209, American Chemical Society, Washington (1998)

Loeper et al "Hypotensive action of tincture of garlic", *Progress Medical* 36:391–392 (1921)( Malik et al, "Hypotensive effect of freeze-dried garlic (*Allium Sativum*) sap in dog", *PMA J Pak Med Assoc* 31:12–13 (1981)

Materson et al, "Angiotensin-converting enzyme inhibitors in hypertension. A dozen years of experience", *Arch Intern Med* 1544:513–523(1994)

Migdalof et al, "Captopril: pharmacology, metabolism and disposition", *Drug Metab Rev* 15:841–869 (1984)

Mirelman et al, WO 97/39115, "Immoblized Alliinase and Continuous Production of Allicin", Oct. 23, 1997

Miron et al "The mode of action of allicin: its ready permeability through phospholipid membranes may contribute to its biological activity", *Biochim Bioiphys Acta* 1463:20–30 (2000)

Ondetti et al, "Design of specific inhibitors of angiotensin-converting enzyme: new class of orally active antihypertensive agents", *Science* 196:441–444 (1977)

Ondetti et al, U.S. Pat. No. 4,046,889, "Azetidine-2-carboxylic acid derivatives", Sep. 6, 1977

Petkov U, "Plants with hypotensive, antiatheromatous and coronarodilating action", *Am J of Chinese Medicine* 7:197–236 (1979)

Rabinkov et al "The mode of action of allicin: trapping of radicals and interaction with thiol contaiing proteins", *Biochim Biophys Acta* 1379:233–244 (1998)

Reaven et al, "Sugar-induced hypertension in Sprague-Dawley rats", *Am J Hypertens* 4(7 Pt 1):610–614(1991)

Ruffin et al, "An evaluation of the side effects of garlic as an antihypertensive agent", *Cytobios* 37(146):85–89 (1983)

Thind. G S, "Angiotensin converting enzyme inhibitors: comparative structure, pharmacokinetics, and pharmacodynamics", *Cardiovase Drugs Ther* 4:199–206 (1990)

What is claimed is:

1. A compound of the formula:

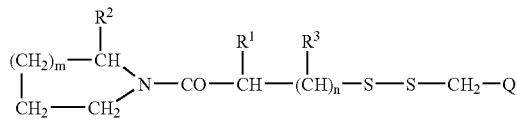

where
  $R^1$ is hydrogen, lower alkyl or phenyl-lower alkyl;
  $R^2$ is hydrogen, hydroxy, lower alkyl, $R_3CO$, or carboxyl;

R³ is hydrogen, lower alkyl or phenyl-lower alkyl;
m is 0–10;
n is 0, 1, or 2; and
Q is —CH═CH₂ or —C≡CH.

2. The compound according to claim 1, wherein m is 1 to 5.

3. The compound according to claim 1, wherein R¹ is hydrogen or lower alkyl; R² and R³ are each hydrogen.

4. The compound according to claim 1, wherein R² and R³ are each hydrogen.

5. The compound according to claim 1, wherein R² is hydrogen.

6. The L-form of the compound of claim 1.

7. The compound according to claim 1, wherein n is 1.

8. The compound according to claim 1, wherein R¹ is hydrogen or lower alkyl.

9. The compound according to claim 1, wherein R¹ is hydrogen or methyl.

10. The compound according to claim 1, wherein n is 0.

11. The compound according to claim 7, wherein R¹, R², and R³ are each hydrogen.

12. The compound according to claim 7, wherein R¹ is methyl and R² and R³ are each hydrogen.

13. The compound according to claim 11, wherein m is 1 and the compound is in the L-form.

14. The compound according to claim 12, wherein m is 1 and the compound is in the L-form.

15. The compound according to claim 1, wherein Q is —C═CH₂.

16. The compound according to claim 1, wherein Q is —C≡CH.

17. A method for treating hypertension comprising administering to a patient in need thereof an effective amount of a compound according to claim 1.

18. A pharmaceutical composition for treating hypertension comprising an effective amount to reduce blood pressure of at least one compound according to claim 1 and a pharmaceutically acceptable carrier.

19. A method for preparing a compound in accordance with claim 1, comprising reacting an ACE-inhibiting proline derivative compound containing a free thiol group, of the formula

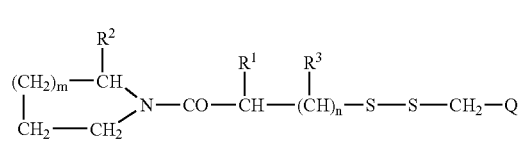

with allicin or a derivative thereof of the formula

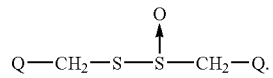

20. The method according to claim 19, wherein the ACE-inhibiting proline derivative compound with a free thiol group is captopril.

21. A method for treating elevated triglycerides comprising administering to a patient in need thereof an effective amount of a compound according to claim 1.

22. A method for treating elevated insulin levels comprising administering to a patient in need thereof an effective amount of a compound according to claim 1.

* * * * *